(12) United States Patent
Mansour et al.

(10) Patent No.: US 10,653,879 B2
(45) Date of Patent: May 19, 2020

(54) NEEDLELESS CONNECTOR WITH COMPRESSIBLE VALVE

(71) Applicant: CareFusion 303, Inc., San Diego, CA (US)

(72) Inventors: George Michel Mansour, Pomona, CA (US); Christopher J. Zollinger, Chino Hills, CA (US); Matthew Quach, San Gabriel, CA (US); Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 16/027,192

(22) Filed: Jul. 3, 2018

(65) Prior Publication Data

US 2018/0311491 A1 Nov. 1, 2018

Related U.S. Application Data

(63) Continuation of application No. 14/868,180, filed on Sep. 28, 2015, now Pat. No. 10,016,588, which is a (Continued)

(51) Int. Cl.
*A61M 39/26* (2006.01)
*A61M 39/10* (2006.01)
(Continued)

(52) U.S. Cl.
CPC ............ *A61M 39/26* (2013.01); *A61M 39/10* (2013.01); *A61M 39/22* (2013.01); *A61M 39/24* (2013.01); *A61M 2039/2433* (2013.01)

(58) Field of Classification Search
CPC ...... A61M 39/26; A61M 39/24; A61M 39/22; A61M 39/10; A61M 2039/2433
See application file for complete search history.

(56) References Cited

U.S. PATENT DOCUMENTS

| 3,192,949 A | 7/1965 | De See |
| 4,141,379 A | 2/1979 | Manske |

(Continued)

FOREIGN PATENT DOCUMENTS

| CN | 1077654 A | 10/1993 |
| CN | 1139010 A | 1/1997 |

(Continued)

OTHER PUBLICATIONS

Australian Office Action for Application No. 2018278973, dated Aug. 9, 2019, 4 pages.

(Continued)

*Primary Examiner* — Amber R Stiles
(74) *Attorney, Agent, or Firm* — Morgan, Lewis & Bockius LLP

(57) ABSTRACT

Needleless connectors are described. An example needleless connector includes a housing and a compressible valve. The housing may define an internal cavity and may include a body section having a first port and one or more internal contact tabs and a base section having a valve mount and a second port. The compressible valve may be disposed within at least a portion of the internal cavity and be movably retained within the housing. The compressible valve may include a flange portion for securing the compressible valve within the housing. A central longitudinal axis of the housing may be defined by a coaxial arrangement of the first and second port. The one or more internal contact tabs may be arranged to contact an outer side surface of the flange portion such that a radial force substantially orthogonal to the central longitudinal axis is provided for securement.

20 Claims, 13 Drawing Sheets

Related U.S. Application Data continuation of application No. 14/149,753, filed on Jan. 7, 2014, now Pat. No. 9,144,672, and a continuation-in-part of application No. 13/829,227, filed on Mar. 14, 2013, now Pat. No. 8,840,577, and a continuation-in-part of application No. 13/829,187, filed on Mar. 14, 2013, now Pat. No. 9,089,682, and a continuation-in-part of application No. 13/801,422, filed on Mar. 13, 2013, now Pat. No. 9,370,651, and a continuation-in-part of application No. 13/801,412, filed on Mar. 13, 2013, now abandoned, and a continuation-in-part of application No. 13/801,399, filed on Mar. 13, 2013, now Pat. No. 9,278,205.

(51) Int. Cl.
*A61M 39/22* (2006.01)
*A61M 39/24* (2006.01)

(56) References Cited

U.S. PATENT DOCUMENTS

| | | |
|---|---|---|
| 4,535,820 A | 8/1985 | Raines |
| 4,654,031 A | 3/1987 | Lentz |
| 4,712,583 A | 12/1987 | Pelmulder et al. |
| 4,911,403 A | 3/1990 | Lockwood, Jr. |
| 5,092,857 A | 3/1992 | Fleischhacker |
| 5,242,432 A | 9/1993 | DeFrank |
| 5,401,255 A | 3/1995 | Sutherland et al. |
| 5,439,451 A | 8/1995 | Collinson et al. |
| 5,549,651 A | 8/1996 | Lynn |
| 5,555,908 A | 9/1996 | Edwards et al. |
| 5,613,663 A | 3/1997 | Schmidt et al. |
| 5,623,969 A | 4/1997 | Raines |
| 5,690,612 A | 11/1997 | Lopez et al. |
| 5,699,821 A | 12/1997 | Paradis |
| 5,730,418 A | 3/1998 | Feith et al. |
| 5,782,816 A | 7/1998 | Werschmidt et al. |
| 5,992,462 A | 11/1999 | Atkinson et al. |
| 5,996,631 A | 12/1999 | Thronton |
| 6,024,729 A | 2/2000 | Dehdashtian et al. |
| 6,050,978 A | 4/2000 | Orr et al. |
| 6,245,048 B1 | 6/2001 | Fangrow, Jr. et al. |
| 6,679,219 B1 | 1/2004 | Pacinelli |
| 6,883,778 B1 | 4/2005 | Newton et al. |
| 6,886,803 B2 | 5/2005 | Mikiya et al. |
| 7,184,825 B2 | 2/2007 | Leinsing et al. |
| 7,360,556 B2 | 4/2008 | Mijers |
| 7,789,864 B2 | 9/2010 | Cote, Sr. et al. |
| 7,887,519 B2 | 2/2011 | Cote, Sr. et al. |
| 7,971,804 B2 | 7/2011 | Roberts |
| 8,062,261 B2 | 11/2011 | Adams |
| 8,291,936 B2 | 10/2012 | Carmody et al. |
| 8,568,371 B2 | 10/2013 | Siopes et al. |
| 8,720,065 B2 | 5/2014 | Christensen et al. |
| 9,089,682 B2 | 7/2015 | Yeh et al. |
| 9,138,572 B2 | 9/2015 | Zeytoonian et al. |
| 2002/0002351 A1* | 1/2002 | Cote, Sr. ............... A61M 39/26 604/247 |
| 2002/0133124 A1 | 9/2002 | Leinsing et al. |
| 2002/0193752 A1 | 12/2002 | Lynn |
| 2003/0050610 A1 | 3/2003 | Newton et al. |
| 2003/0098430 A1 | 5/2003 | Leinsing et al. |
| 2004/0227120 A1 | 11/2004 | Raybuck |
| 2005/0059952 A1 | 3/2005 | Giuliano et al. |
| 2005/0222541 A1 | 10/2005 | Lopez et al. |
| 2006/0025724 A1 | 2/2006 | Chen |
| 2006/0027270 A1 | 2/2006 | Truitt et al. |
| 2006/0089603 A1 | 4/2006 | Truitt et al. |
| 2006/0163515 A1* | 7/2006 | Ruschke ............... A61M 39/26 251/149.7 |
| 2006/0208210 A1 | 9/2006 | Raybuck |
| 2007/0270756 A1 | 11/2007 | Peppel et al. |
| 2008/0108956 A1 | 5/2008 | Lynn et al. |
| 2009/0030401 A1 | 1/2009 | Phillips |
| 2009/0057589 A1 | 3/2009 | Thorne, Jr. et al. |
| 2009/0299300 A1* | 12/2009 | Truitt ............... A61M 39/02 604/246 |
| 2010/0036330 A1 | 2/2010 | Plishka et al. |
| 2010/0234798 A1 | 9/2010 | Huang |
| 2010/0256573 A1 | 10/2010 | Mansour et al. |
| 2011/0028914 A1 | 2/2011 | Mansour et al. |
| 2011/0028915 A1* | 2/2011 | Siopes ............... A61M 39/26 604/256 |
| 2011/0046573 A1 | 2/2011 | Newton et al. |
| 2011/0130724 A1 | 6/2011 | Mansour et al. |
| 2011/0152787 A1 | 6/2011 | Truitt et al. |
| 2012/0310179 A1 | 12/2012 | Truitt et al. |
| 2012/0316514 A1 | 12/2012 | Mansour |
| 2013/0030386 A1 | 1/2013 | Panian et al. |
| 2013/0190684 A1 | 7/2013 | Panian et al. |

FOREIGN PATENT DOCUMENTS

| | | |
|---|---|---|
| CN | 1305391 A | 7/2001 |
| CN | 102481445 A | 5/2012 |
| CN | 102497897 A | 6/2012 |
| CN | 102686265 A | 9/2012 |
| EP | 2075032 A1 | 7/2009 |
| EP | 2411085 A2 | 2/2012 |
| EP | 2719419 A1 | 4/2014 |
| JP | H0857058 A | 3/1996 |
| JP | H09182790 A | 7/1997 |
| JP | 2002514475 A | 5/2002 |
| JP | 2005511162 A | 4/2005 |
| JP | 2007500537 A | 1/2007 |
| JP | 2008517653 A | 5/2008 |
| JP | 2008522729 A | 7/2008 |
| JP | 2008264030 A | 11/2008 |
| JP | 2009148561 A | 7/2009 |
| JP | 366779 U | 3/2011 |
| JP | 2011147809 A | 8/2011 |
| JP | 20125605 A | 1/2012 |
| JP | 201224565 A | 2/2012 |
| JP | 2012530555 A | 12/2012 |
| JP | 2013500128 A | 1/2013 |
| JP | 2013022415 A | 2/2013 |
| WO | WO-9826835 A1 | 6/1998 |
| WO | WO-2004082756 A1 | 9/2004 |
| WO | WO-2004112866 A2 | 12/2004 |
| WO | WO-2005011799 A1 | 2/2005 |
| WO | WO-2006078355 A1 | 7/2006 |
| WO | WO-2008091698 A2 | 7/2008 |
| WO | WO-2010151507 A1 | 12/2010 |
| WO | WO-2011014265 A1 | 2/2011 |
| WO | WO-2011060384 A1 | 5/2011 |
| WO | WO-2011119347 A2 | 9/2011 |
| WO | WO-2013016077 A2 | 1/2013 |
| WO | WO-2013099261 A1 | 7/2013 |
| WO | WO-2013122148 A1 | 8/2013 |

OTHER PUBLICATIONS

Australian Office Action for Application No. 2019201757, dated Aug. 1, 2019, 2 pages.
Australian Examination Report No. 1 for Application No. 2014228543, dated Sep. 26, 2017, 2 pages.
Australian Examination Report No. 1 for Application No. 2014228618, dated Aug. 30, 2017, 3 pages.
Australian Examination Report No. 1 for Application No. 2014228626, dated Aug. 4, 2017, 3 pages.
Australian Examination Report No. 1 for Application No. 2014242176, dated Sep. 5, 2017, 2 pages.
Australian Examination Report No. 1 for Application No. 2014248948, dated Feb. 28, 2018, 4 pages.
Australian Examination Report No. 2 for Application No. 2014242176, dated Apr. 16, 2018, 3 pages.
Australian Examination Report No. 2 for Application No. 2014248948, dated Jul. 16, 2018, 4 pages.
Australian Examination Report No. 1 for Application No. 2014228627, dated Mar. 14, 2018, 3 pages.

(56) References Cited

OTHER PUBLICATIONS

Chinese Office Action for Application No. 201480014352.0, dated Feb. 2, 2018, 5 pages.
Chinese Office Action for Application No. 2014800143520, dated Dec. 5, 2016, 7 pages.
Chinese Office Action for Application No. 201480014557.9, dated Apr. 10, 2018, 8 pages.
Chinese Office Action for Application No. 201480014557.9, dated Mar. 3, 2017, 6 pages.
Chinese Office Action for Application No. 201480014965.4, dated Mar. 3, 2017, 9 pages.
Chinese Office Action for Application No. 201480014971.X, dated Feb. 21, 2017, 6 pages.
Chinese Office Action for Application No. 201480015027.6, dated Mar. 10, 2017, 7 pages.
Chinese Office Action for Application No. 201480015065.1, dated Feb. 22, 2017, 7 pages.
Chinese Second Office Action for 201480014352.0, dated Jun. 21, 2017, 7 pages.
Chinese Second Office Action for Application No. 201480014557.9, dated Oct. 23, 2017, 8 pages.
Chinese Second Office Action for Application No. 201480014965.4, dated Oct. 23, 2017, 3 pages.
Chinese Second Office Action for Application No. 201480014971.X, dated Aug. 16, 2017, 3 pages.
Chinese Second Office Action for Application No. 201480015065.1, dated Sep. 8, 2017, 3 pages.
Chinese Third Office Action for Application No. 2014800143520, dated Sep. 26, 2017, 4 pages.
European Office Action for Application No. 14/708451.1, dated Nov. 30, 2016, 3 pages.
European Office Action for Application No. 14158885.5, dated Dec. 16, 2015, 5 pages.
European Office Action for Application No. 14158899.6, dated Sep. 13, 2017, 4 pages.
European Office Action for Application No. 14708450.3, dated Oct. 25, 2017, 4 pages.
European Office Action for Application No. 14709077.3, dated Sep. 19, 2017, 6 pages.
Extended European Search Report and Written Opinion for Application No. 17158061.6, dated Jun. 20, 2017, 7 pages.
Extended European Search Report for Application No. 14778965.5, dated May 9, 2017, 13 pages.
Extended European Search Report for Application No. 18155594.7, dated May 15, 2018, 8 pages.
Extended European Search Report in European Application No. 14158882.2 dated Jul. 7, 2014, 7 pages.
Extended European Search Report in European Application No. 14158885.5 dated May 12, 2014, 11 pages.
Extended European Search Report in European Application No. 14158891.3 dated Jul. 8, 2014, 6 pages.
Extended European Search Report in European Application No. 14158894.7 dated May 12, 2014, 8 pages.
Extended European Search Report in European Application No. 14158899.6 dated Jul. 8, 2014, 6 pages.
International Search Report and Written Opinion in PCT Application No. PCT/US2014/017480 dated May 13, 2014, 13 pages.
International Search Report and Written Opinion in PCT Application No. PCT/US2014/017486 dated May 13, 2014, 14 pages.
International Search Report and Written Opinion in PCT Application No. PCT/US2014/017824 dated May 9, 2014, 21 pages.
International Search Report and Written Opinion in PCT Application No. PCT/US2014/017826 dated May 8, 2014, 10 pages.
International Search Report and Written Opinion in PCT Application No. PCT/US2014/017828 dated May 2, 2014, 10 pages.
International Search Report and Written Opinion in PCT Application No. PCT/US2014/023694 dated Jun. 26, 2014, 11 pages.
International Written Opinion of the International Preliminary Examining Authority for International Application No. PCT/US2014/017824, dated Mar. 23, 2015, 6 pages.
International Written Opinion of the International Preliminary Examining Authority for International Application No. PCT/US2014/017828, dated Mar. 20, 2015, 6 pages.
Japanese Office Action for Application No. 2016-500315, dated Mar. 9, 2018, 3 pages.
Japanese Office Action for Application No. 2016-500315, dated Nov. 24, 2017, 2 pages.
Japanese Office Action for Application No. 2016-500317, dated Oct. 25, 2017, 4 pages.
Japanese Office Action for Application No. 2016-500341, dated Mar. 9, 2018, 3 pages.
Japanese Office Action for Application No. 2016-500341, dated Nov. 24, 2017, 2 pages.
Japanese Office Action for Application No. 2016-500342, dated Nov. 28, 2017, 4 pages.
Japanese Office Action for Application No. 2016-500343, dated Dec. 21, 2017, 3 pages.
Japanese Office Action for Application No. 2016-500343, dated Jul. 17, 2018, 2 pages.
Japanese Office Action for Application No. 2016-501317, dated Jan. 16, 2018, 5 pages.
Partial Supplementary European Search Report for Application No. 14778965.5, dated Dec. 16, 2016, 7 pages.
Chinese Office Action for Application No. 201480014557.9, dated Jan. 23, 2019, 11 pages.
Australian Office Action for Application No. 2018214010, dated Aug. 1, 2019, 2 pages.
India Office Action for Application No. 3149/KOLNP/2015, dated Jul. 29, 2019, 5 pages.
India Office Action for Application No. 3248/KOLNP/2015, dated Jul. 30, 2019, 5 pages.
Japanese Office Action for Application No. 2018-145746, dated Jul. 2, 2019, 8 pages.
India Office Action for Application No. 2780/KOLNP/2015 dated Sep. 17, 2019, 8 pages.
India Office Action for Application No. 3370/KOLNP/2015, dated Sep. 26, 2019, 8 pages.
Japanese Office Action for Application No. 2018-223368, dated Oct. 29, 2019, 7 pages.
Canadian Office Action for Application No. 2901772, dated Dec. 16, 2019, 3 pages.
Canadian Office Action for Application No. 2901177, dated Dec. 6, 2019, 3 pages.
Canadian Office Action for Application No. 2901180, dated Dec. 9, 2019, 3 pages.
Canadian Office Action for Application No. 2901592, dated Dec. 17, 2019, 6 pages.
Canadian Office Action for Application No. 2901673, dated Dec. 11, 2019, 3 pages.
European Office Action for Application No. 14158899.6, dated Feb. 12, 2020, 5 pages.
Extended European Search Report for Application No. 20153180.3, dated Feb. 19, 2020, 7 pages.
India Office Action for Application No. 2764/KOLNP/2015, dated Feb. 5, 2020, 8 pages.

* cited by examiner

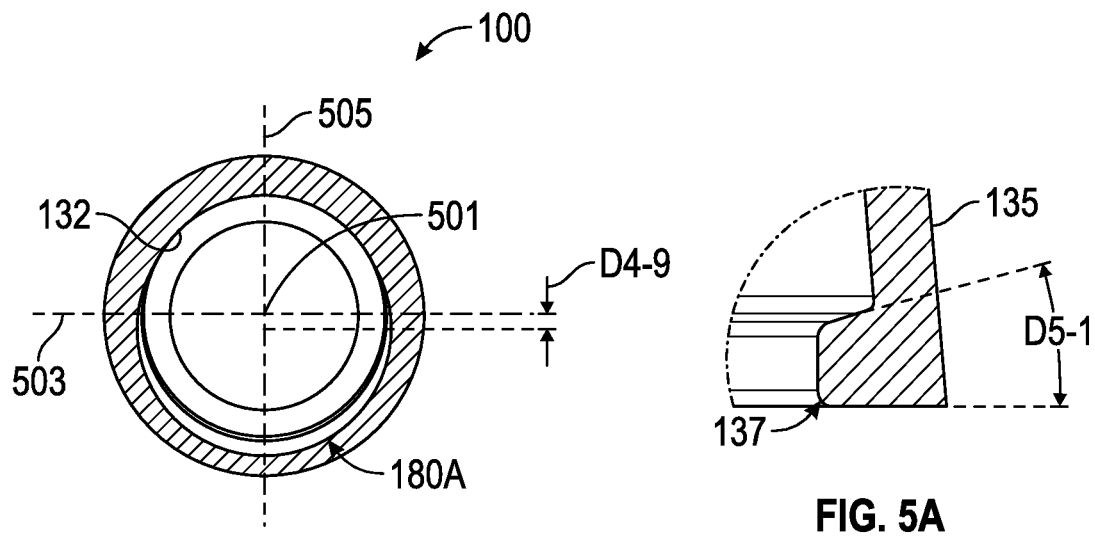
FIG. 4B
FIG. 5A
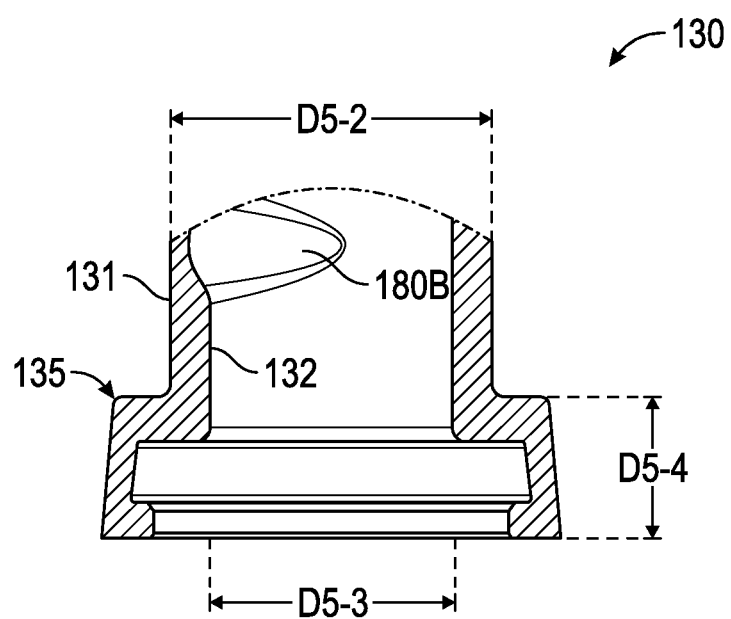
FIG. 5B

NEEDLELESS CONNECTOR WITH COMPRESSIBLE VALVE

CROSS-REFERENCE TO RELATED APPLICATIONS

This application is a continuation of U.S. patent application Ser. No. 14/868,180, entitled "NEEDLELESS CONNECTOR WITH COMPRESSIBLE VALVE," filed Sep. 28, 2015, which is a continuation of U.S. patent application Ser. No. 14/149,753, entitled "NEEDLELESS CONNECTOR WITH COMPRESSIBLE VALVE," filed Jan. 7, 2014, now U.S. Pat. No. 9,144,672, which is a continuation-in-part and claims the benefit of U.S. patent application Ser. No. 13/801,399, entitled "COLLAPSIBLE VALVE WITH INTERNAL DIMPLES," filed on Mar. 13, 2013, now U.S. Pat. No. 9,278,205, which is a continuation-in-part and claims the benefit of U.S. patent application Ser. No. 13/801,412, entitled "NEEDLELESS CONNECTOR WITH FOLDING VALVE," filed on Mar. 13, 2013, which is a continuation-in-part and claims the benefit of U.S. patent application Ser. No. 13/829,227, entitled "NEEDLELESS CONNECTOR WITH FLEXIBLE VALVE," filed on Mar. 14, 2013, now U.S. Pat. No. 8,840,577, which is a continuation-in-part and claims the benefit of U.S. patent application Ser. No. 13/829,187, entitled "NEEDLELESS CONNECTOR WITH SUPPORT MEMBER," filed on Mar. 14, 2013, now U.S. Pat. No. 9,089,682, and is a continuation-in-part and claims the benefit of U.S. patent application Ser. No. 13/801,422, entitled "NEEDLELESS CONNECTOR WITH REDUCED TRAPPED VOLUME," filed on Mar. 13, 2013, now U.S. Pat. No. 9,370,651, each of which is hereby incorporated by reference in its entirety for all purposes.

BACKGROUND

The present disclosure generally relates to needleless connectors, and more particularly to needleless connectors with valves.

Medical treatments often include the infusion of a medical fluid, for example a saline solution or a liquid medication, to patients using an intravenous (IV) catheter that is connected though an arrangement of flexible tubing and fittings, commonly referred to as an "IV set," to a source of fluid, for example an IV bag. The fittings commonly include interconnectable male and female needleless connectors having a "Luer taper" conforming to an International Standards Organization (ISO) standard. Certain connectors have a self-sealing feature to prevent leakage of fluid from the attached tubing when the connector is decoupled from a mating connector.

SUMMARY

In accordance with certain embodiments, a needleless connector may be self-sealing and include a female Luer connector for engagement with a medical implement. The needleless connector may be reduced in size compared to conventional connectors and, therefore, a reduced amount of fluid may be trapped, if any, within the needleless connector upon disconnection of the medical implement. The connector also accepts a standard male Luer fitting and provides a self-sealing port with a continuous external surface at the port when the connector is not activated such that the port may be disinfected prior to or after use.

The disclosed needleless connector overcomes many challenges discovered with respect to certain conventional connectors. For example, certain conventional needleless self-sealing connectors are relatively large and require a significant axial force on the valve element to activate the connector. This axial force may cause stress on a fused connection of the housing that houses the valve element. As certain types of medical fluids may degrade within a treatment time period, retention of medical fluid within the connector is undesirable and may be exacerbated with larger conventional connectors. For example, build-up of certain medical fluids may cause occlusions that may impair the functionality of the connector and/or hazardously release such occlusions into the IV set.

Therefore, in accordance the present disclosure, it is advantageous to provide a disclosed needleless connector that overcomes these challenges. In addition, various arrangements and features of the compressible valve and housing of the disclosed needleless connectors are provided for improved operation and longevity of the device.

The subject technology is illustrated, for example, according to various aspects described below. Various examples of aspects of the subject technology are described as numbered clauses or embodiments (1, 2, 3, etc.) for convenience. These are provided as examples and do not limit the subject technology. It is noted that any of the dependent clauses may be combined in any combination with each other or one or more other independent clauses, to form an independent clause. The other clauses can be presented in a similar manner. The following is a non-limiting summary of some embodiments presented herein:

Clause 1. A needleless connector comprising: a housing defining an internal cavity and a central longitudinal axis, the housing comprising a body section and a base section, the body section comprising a first port, and the base section comprising a valve mount at a top of the base section and a second port at a bottom of the base section, the valve mount comprising an upper wall, a lower wall, and a valve mount rim, wherein the upper and lower walls extend from the valve mount rim toward the central longitudinal axis; and a compressible valve comprising a valve wall and a flange protruding radially outward from an outer surface of the valve wall, the flange comprising an outer surface and an inner surface forming a channel, wherein, when the compressible valve is coupled with the valve mount, the valve mount rim extends into the channel.

Clause 2. The needleless connector of Clause 1, wherein the channel extends into the inner surface, toward the outer surface of the flange.

Clause 3. The needleless connector of Clause 1, wherein the body section comprises an inner contact tab extending into the internal cavity, and, when the compressible valve is coupled with the valve mount and the body section, at least a portion of the flange is positioned between the valve mount and the contact tab.

Clause 4. The needleless connector of Clause 1, wherein the valve wall comprises a first dimple and a second dimple formed in an internal surface.

Clause 5. The needleless connector of Clause 1, wherein base section comprises a recess between the valve mount and the second port.

Clause 6. The needleless connector of Clause 5, wherein support members extend laterally inward from the valve mount into the recess.

Clause 7. The needleless connector of Clause 5, wherein the body section comprises an inner support column.

Clause 8. The needleless connector of Clause 5, wherein the valve mount rim extends from the upper wall toward the bottom of the base section.

Clause 9. A needleless connector comprising: a housing defining an internal cavity and a central longitudinal axis, the housing comprising a body section and a base section, the body section comprising a first port, and the base section comprising a valve mount at a top of the base section and a second port at a bottom of the base section, the valve mount comprising an upper wall, a lower wall, and a valve mount rim; and a compressible valve comprising a valve wall and a flange protruding radially outward from an outer surface of the valve wall, the flange comprising an upper lip, a lower lip, and a flange rim, wherein, when the compressible valve is coupled with the valve mount, the lower lip extends along the lower wall toward the central longitudinal axis.

Clause 10. The needleless connector of Clause 9, wherein the lower lip is spaced apart from the upper lip.

Clause 11. The needleless connector of Clause 9, wherein a channel is formed between an inner surface of the upper lip and an inner surface of the lower lip.

Clause 12. The needleless connector of Clause 9, wherein an outer surface of the flange rim tapers from the lower lip toward the upper lip.

Clause 13. The needleless connector of Clause 9, wherein a height of the lower lip taper toward the central longitudinal axis.

Clause 14. The needleless connector of Clause 9, wherein the body section comprises an inner contact tab extending into the internal cavity, and, when the compressible valve is coupled with the valve mount and the body section, at least a portion of the flange is positioned between the valve mount and the contact tab.

Clause 15. The needleless connector of Clause 9, wherein the valve wall comprises a first dimple and a second dimple formed in an internal surface.

Clause 16. The needleless connector of Clause 9, wherein base section comprises a recess between the valve mount and the second port.

Clause 17. The needleless connector of Clause 16, wherein support members extend laterally inward from the valve mount into the recess.

Clause 18. The needleless connector of Clause 17, wherein the support members extend between the upper wall and a bottom surface of the recess.

Clause 19. The needleless connector of Clause 9, wherein the body section comprises an inner support column.

Clause 20. The needleless connector of Clause 9, wherein the valve mount rim extends from the upper wall toward the bottom of the base section.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 4B is a cross-sectional view illustrating an example of a dimple disposed on an interior surface of a compressible valve, in accordance with aspects of the present disclosure.

FIGS. 5A and 5B are enlarged cross-sectional views illustrating example sections of a compressible valve, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical professional using an IV set utilized the disclosed needleless connectors, it is to be understood that this description is only an example of usage and does not limit the scope of the claims. Various aspects of the disclosed needleless connectors may be used in any application where it is desirable to avoid blocking a fluid pathway.

Figure 1:
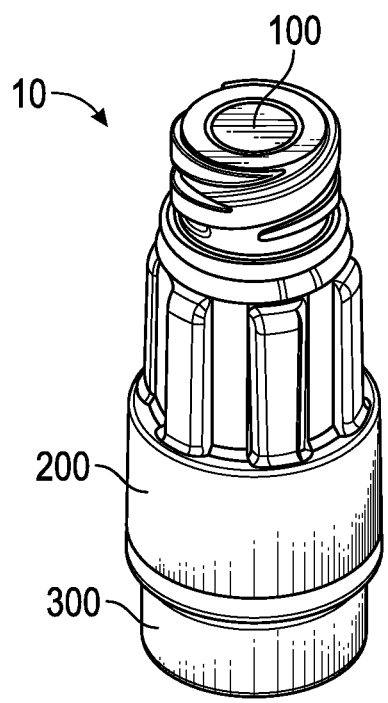
FIG. 1 is a perspective view illustrating an example of a needleless connector, in accordance with aspects of the present disclosure.
Figure 2A:
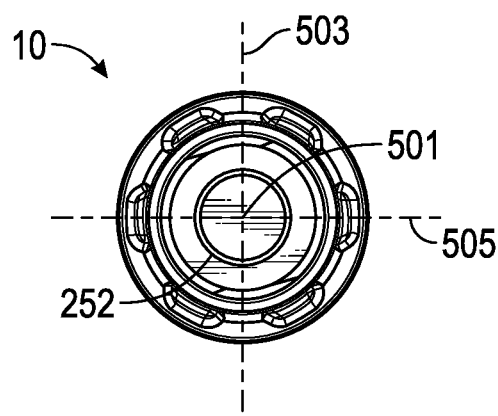
FIG. 2A is a top plan view illustrating an example of a needleless connector, in accordance with aspects of the present disclosure.
Figure 2B:
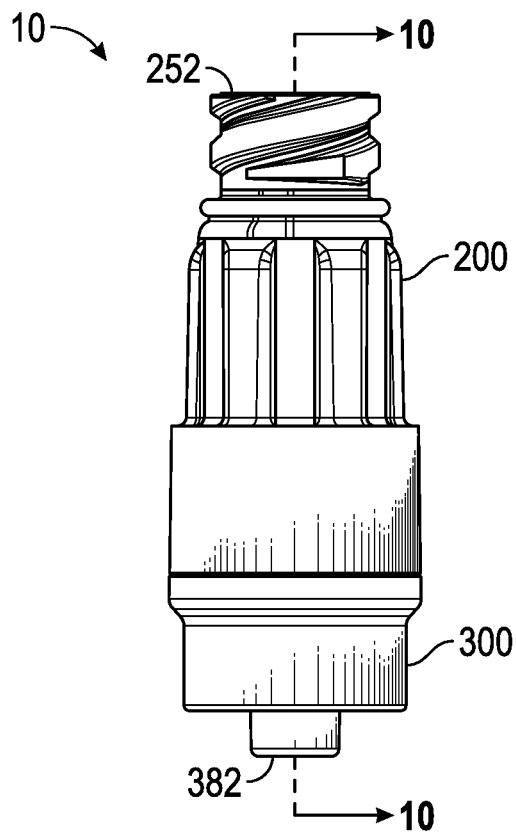
FIG. 2B is a front plan view illustrating an example of a needleless connector, in accordance with aspects of the present disclosure.
Figure 2C:
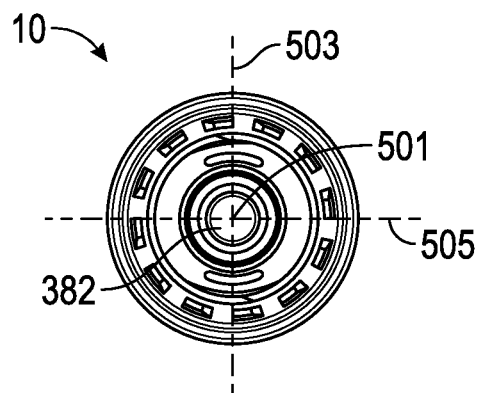
FIG. 2C is a bottom plan view illustrating an example of a needleless connector, in accordance with aspects of the present disclosure.

FIG. 1 is a perspective view of an example needleless connector 10. Needleless connector 10 comprises a housing and a compressible valve 100. The housing may be formed by a body portion 200 and a base portion 300. However, in some embodiments, the housing may be formed from a combination of other pieces or parts similarly dimensioned to house the compressible valve 100 therein. As illustrated in FIGS. 2A, 2B, and 2C, a central longitudinal axis 501 of needleless connector 10 may be defined by orthogonal intersecting planes (plane 503 and plane 505) centrally aligned with respect to a first port 252 of the body portion 200 and a second port 382 of the base portion 300. In operation, a fluid pathway may be established through needleless connector 10 from the first port 252 to the second port 382, for example.

Figure 8A:
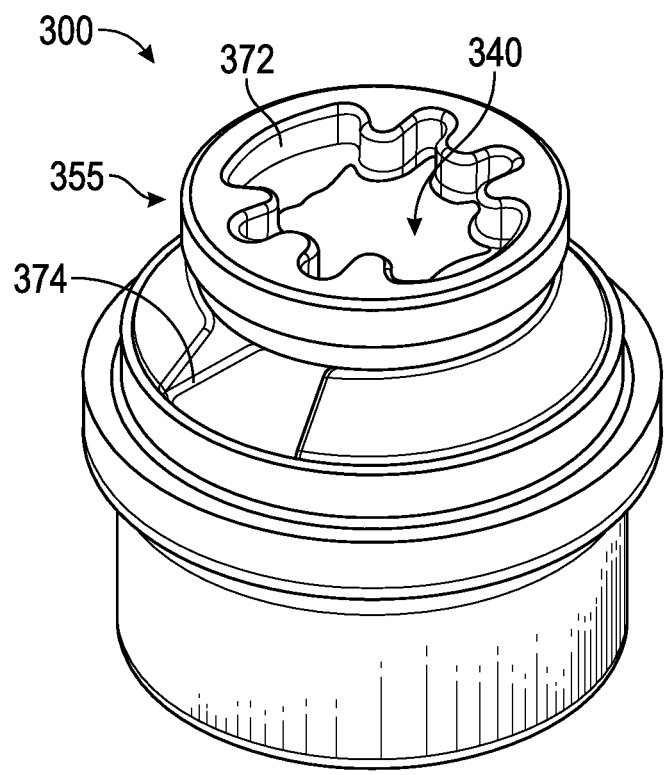
FIGS. 8A and 8B are perspective views illustrating an example of a base portion of a housing, in accordance with aspects of the present disclosure.
Figure 8B:
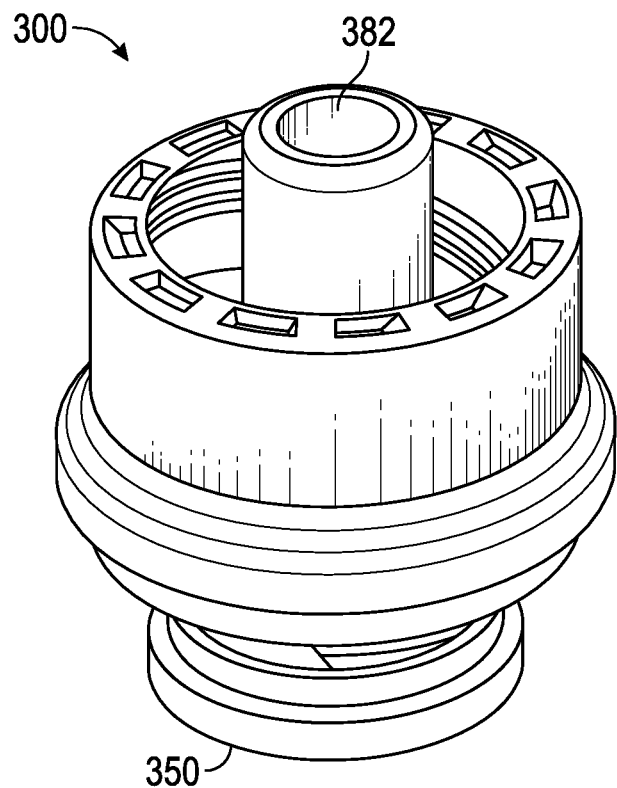
Figure 9A:
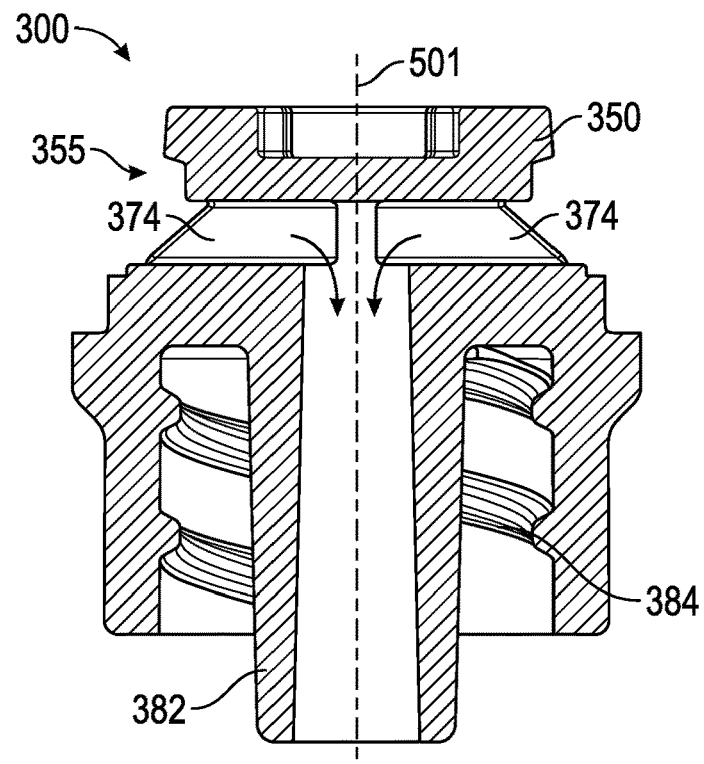
FIGS. 9A and 9B are cross-sectional views illustrating an example of a base portion of a housing, in accordance with aspects of the present disclosure.
Figure 9B:
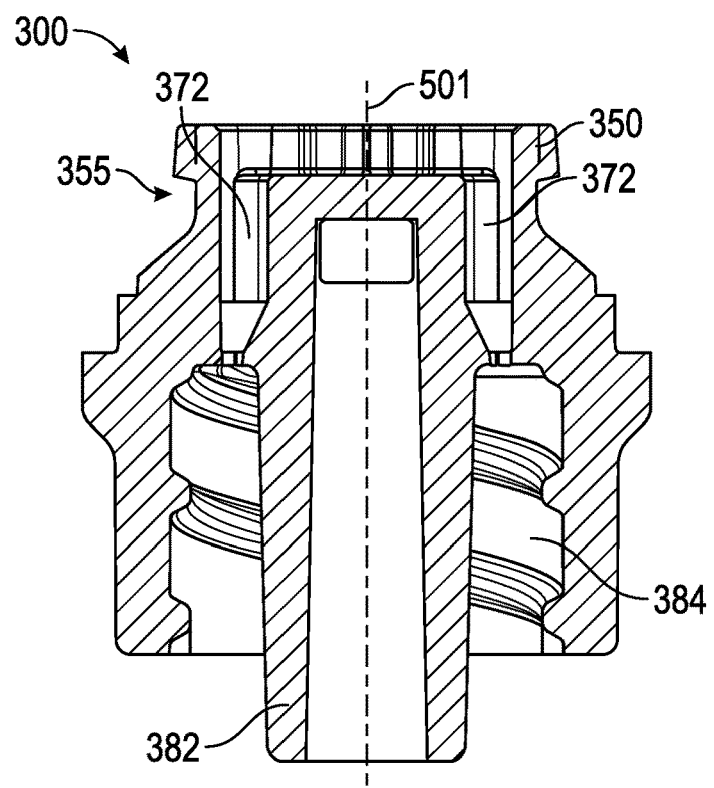
Figure 9C:
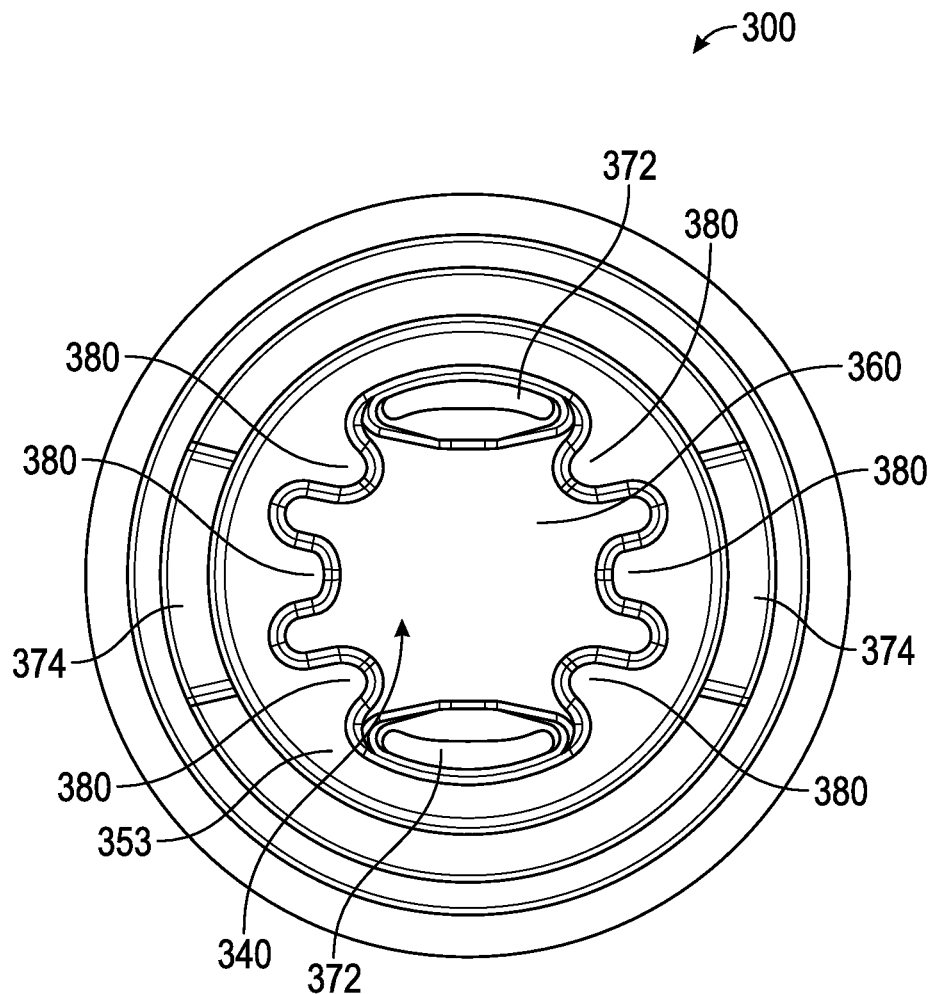
FIG. 9C is a top plan view illustrating an example of a base portion of a housing, in accordance with aspects of the present disclosure.
Figure 10:
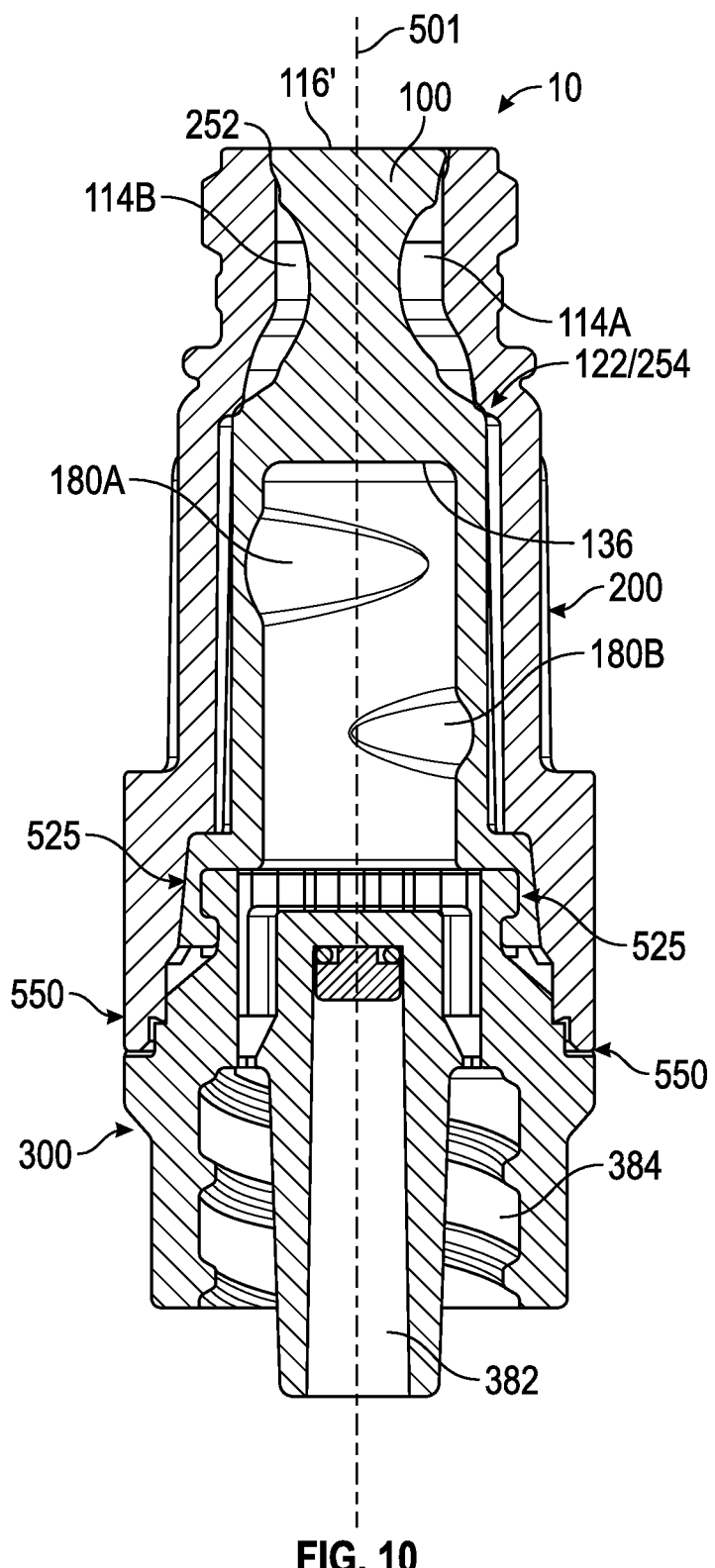
FIG. 10 is a cross-sectional view illustrating an example of a needleless connector, in accordance with aspects of the present disclosure.

A cross-sectional view illustrating a disposition of the compressible valve 100 within the housing of an assembled needleless connector 10 along section line A-A of FIG. 2B is provided in FIG. 10. Various aspects of compressible valve 100, body portion 200, and base portion 300 will first be described in FIGS. 3A through 9C.

Figure 3A:
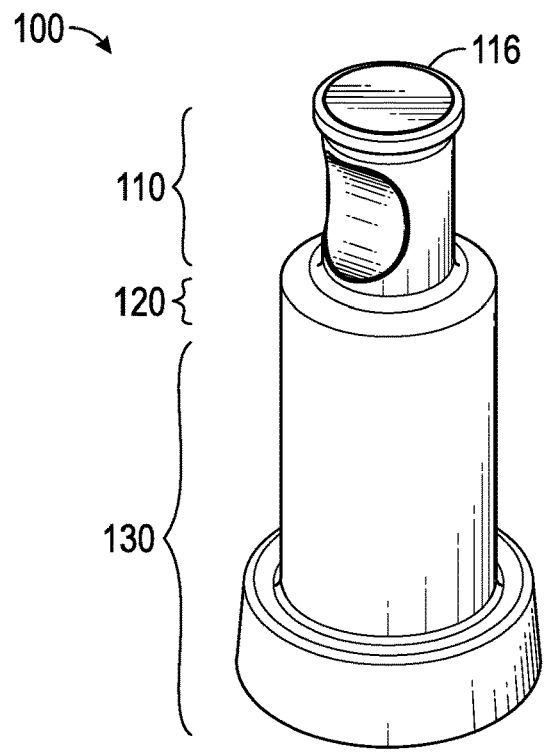
FIG. 3A is a perspective view illustrating an example of a compressible valve, in accordance with aspects of the present disclosure.
Figure 3B:
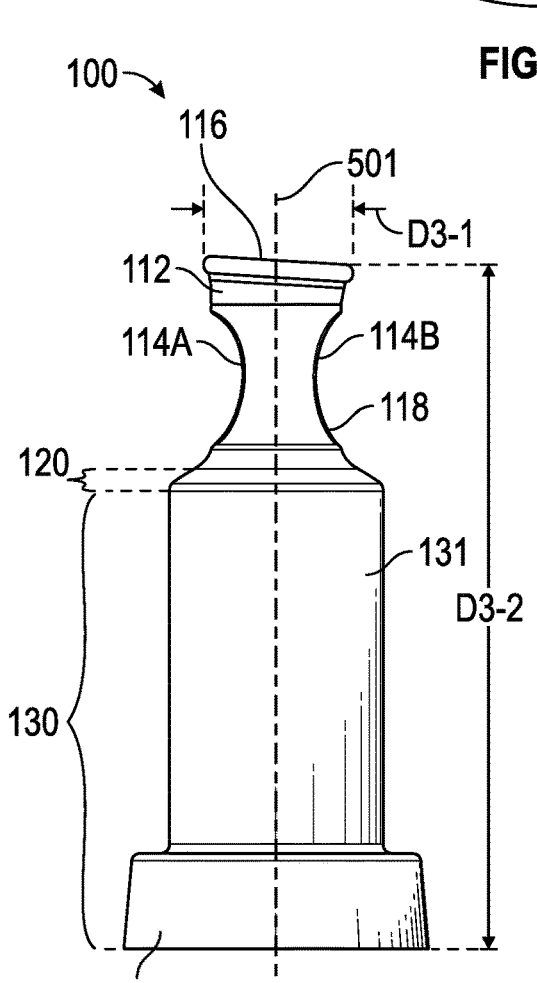
FIGS. 3B and 3C are front plan views illustrating an example of a compressible valve, in accordance with aspects of the present disclosure.
Figure 3C:
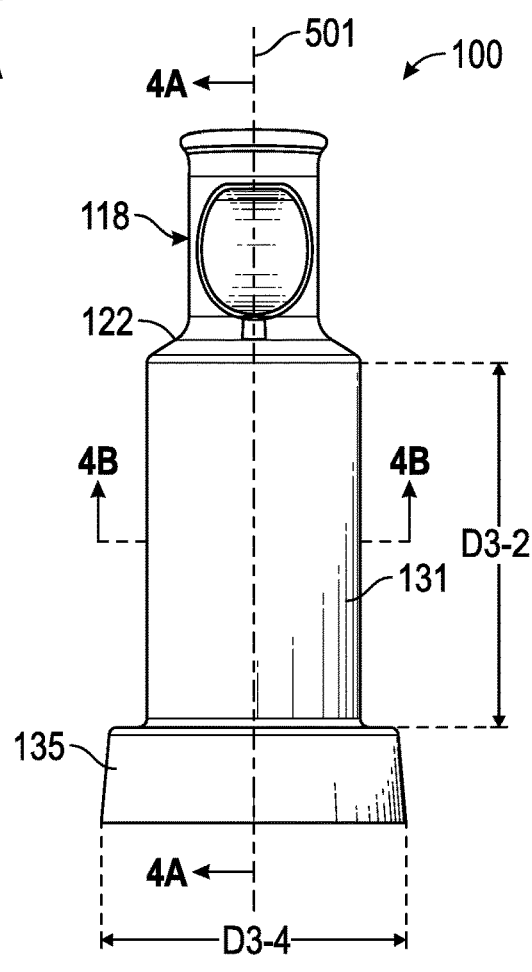

FIGS. 3A to 3C illustrate in isolation an example compressible valve 100. Compressible valve 100 may comprise a head 110, a primary seal portion 120, and a lower portion 130. In certain embodiments, the head 110 comprises a column section 118 having an axial center substantially corresponding to the central longitudinal axis 501 of the needleless connector 10. The central longitudinal axis 501 extends longitudinally through the head 110, primary seal portion 120, and lower portion 130 of the compressible valve 100. However, in some embodiments, the lower portion of the compressible valve 100 may not have the same axial center as the head or other portions of the compressible valve 100. Moreover, the axial centers of compressible valve sections substantially aligned with the central longitudinal axis 501 of the needleless connector 10 are noted with respect to the compressible valve 100 in a non-activated state (e.g., in isolation or within a connector but not displaced by a medical implement). The axial centers of compressible valve sections will change and pivot in relation to the central longitudinal axis 501 upon the compressible valve being activated by a medical implement in certain examples.

The head 110 of the compressible valve 100 comprises a top section 112 that includes a top surface 116. The top surface 116 may be oriented at a non-perpendicular plane angle with respect to the central longitudinal axis 501 as illustrated in FIG. 3B. For example, the top surface 116 can be dimensioned to have a diameter (D3-1) of approximately 0.171 inches. The head 110 comprises at least one notch 114 disposed along the exterior of the column section 118. In certain embodiments, the head 110 may comprise a first notch 114a and a second notch 114b. The first and second notches 114a, 114b may be configured as arcuate-shaped recesses within the column section 118. However, it is to be appreciated that the implementations of notches may comprise a variety of shapes and sizes, such as, but not limited to, notches having arcuate, triangular, polygonal, or various geometric cross-section shapes, for example.

In some embodiments, a head of a compressible valve may not include a notch, but rather has a discontinuity segment disposed on the column section that operates in a similar manner as a notch. For example, one side or a portion of one side of the column section may be comprised of a different material (or a same material with a different hardness value) than the remainder of the column section. Additionally, a side portion of the column section may be hollow (e.g., an internal notch). Thus, an effective change in the resiliency with respect to the movement of the head (similar to that of a removed or extracted volume of a notch) may result and be implemented in some embodiments.

As can be seen form the example embodiments illustrated in FIG. 3A to 3C, the primary seal portion 120 includes a cross-section area greater than a cross-section area of the column section 118 of the head 110. For example, the primary seal portion 120 may comprise a frustoconical surface 122 for engaging with an internal sealing edge of a needleless connector housing. The frustoconical shape of the primary seal portion 120 may be configured such that a first cross-sectional area of the primary seal portion 120 proximal to the head 110 is smaller than a second cross-sectional area of the primary seal portion 120 distally of the head 110 (i.e., where proximally refers to an orientation toward the top surface 116 of the valve 100, and distally refers to an orientation toward the base or bottom of the valve, opposite the top surface 116, as viewed in FIGS. 3A to 3C). In other words, the primary seal portion 120 is narrower towards the head 110 and wider towards the lower portion 130 in certain embodiments.

Lower portion 130 of the compressible valve 100 may comprise an elongated cylindrical wall 131 and a flange portion 135 for securing the compressible valve within the housing. In certain embodiments, the compressible valve 100 can be dimensioned to have a total length (D3-2) from the top surface 116 for the bottom of the flange portion 135 of approximately 0.800 to 0.780 inches. A length (D3-3) of the elongated cylindrical wall 131 can be approximately 0.430 to 0.440 inches and a diameter (D3-4) of the flange portion 135 at its bottommost edge can be approximately 0.350 inches in certain implementations.

Figure 4A:
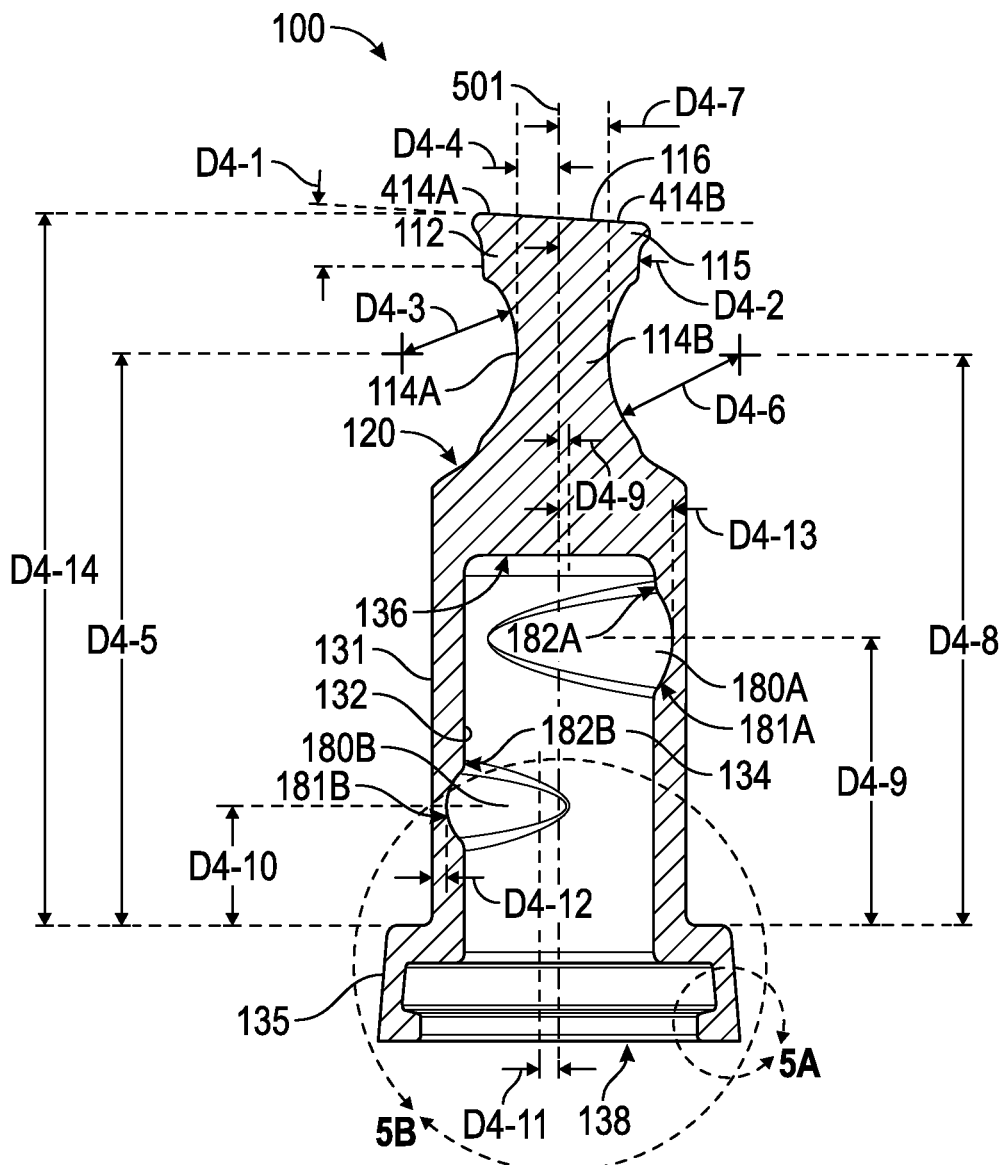
FIG. 4A is a cross-sectional view illustrating an example of a compressible valve, in accordance with aspects of the present disclosure.

FIG. 4A is a longitudinal cross-sectional view of the compressible valve 100 along section line B-B of FIG. 3C. The top surface 116 may include a non-perpendicular plane. In certain embodiments, an angle (D4-1) can be approximately 3° with respect to perpendicular plane to the central longitudinal axis 501. In some embodiments, the top section 112 of the head 110 also includes a circumferential lip 115 or similar protrusion therearound for slidably and sealably engaging with the port channel of the needleless connector housing. A circumferential side of the top section 112 can be dimensioned to have an angle (D4-2) of approximately 9° with respect to the central longitudinal axis 501. A first top edge portion 414a may be defined generally above the first notch 114a and a second top edge portion 414b may be defined generally above the above the second notch 114b (e.g., an arcuate portion of the circumferential edge of the top surface 116 of the top section 112).

In certain embodiments, the first notch 114a has a greater volume than the second notch 114b in reference to the cylindrical shape of the column section 118. In certain implementations, the first notch 114a may be characterized as having an arcuate profile with a radial component having a radius (D4-3) of approximately 0.111 inches extending from a point that is a length (D4-3 and D4-4) of approximately 0.151 inches from the axial center or central longitudinal axis 501 of the compressible valve 100 and a length (D4-5) of approximately 0.550 inches longitudinally from the bottom of the elongated cylindrical wall 131.

Similarly, the second notch 114b may be characterized as having an arcuate profile with a radial component having a radius (D4-6) of approximately 0.125 inches extending from a point that is a length (D4-6 and D4-7) of approximately 0.171 inches from the axial center or central longitudinal axis 501 of the compressible valve 100 and a length (D4-8) of approximately 0.547 inches longitudinally from the bottom of the elongated cylindrical wall 131. In this regard, the first and second notches 114a, 114b may be deemed as being formed with respect to an offset axis parallel to the central longitudinal axis 501 that is a length (D4-9) of approximately 0.010 inches toward the second notch 114b (e.g., a revolve axis offset for the head 110 or upper portion of the compressible valve 100).

Still referring to FIG. 4A, the lower portion 130 of the compressible valve 100 includes a closed end 136 proximal to the primary seal portion 120 and an open end 138 distally of the primary seal portion 120. An interior wall 132 of the lower portion 130 may define, in part, an interior air space 134 of the compressible valve 100. The lower portion 130 may include various interior dimples, incisions, discontinuity segments, or the like disposed along the interior wall 132 to facilitate proper compressing and collapsing functionality in accordance with various embodiments of the present disclosure.

For example, a first interior dimple 180a and a second interior dimple 180b may be disposed on along the interior wall 132. The first interior dimple 180a and the second interior dimple 180b may be disposed on opposite sides of the interior wall 132 and at longitudinally different positions. Moreover, the size and shape of each interior dimple 180a, 180b may be distinct. In certain embodiments, the first interior dimple 180a is larger than the second interior dimple 180b. Moreover, the first notch 114a may be longitudinally aligned with respect to the second internal dimple 180b, and the second notch 114b may be longitudinally aligned with respect to the first interior dimple 180a.

The first interior dimple 180a may be disposed proximal to the primary seal portion 120, and the second interior dimple 180b may be disposed distally of the first interior dimple 180a. Both the first and second interior dimples 180a, 180b may be disposed along the interior wall 132 of the elongated cylindrical wall 131 with respect to the central longitudinal axis 501. In this regard, a lateral center of the first interior dimple 180a may be positioned at a length (D4-9) of approximately 0.275 inches longitudinally from the bottom of the elongated cylindrical wall 131 and a lateral center of the second interior dimple 180b may be positioned at a length (D4-10) of approximately 0.115 inches longitudinally from the bottom of the elongated cylindrical wall 131.

The interior dimples 180a, 180b may be configured to have one or more longitudinal arcuate components for defining elliptically and concaved shaped interior dimples. For example, first interior dimple 180a may comprise a major longitudinal arcuate component 181a and a minor longitudinal arcuate component 182a defining an edge or border of the first interior dimple 180a as shown in FIG. 4A. Similarly, second interior dimple 180b may comprise a major longitudinal arcuate component 181b and a minor longitudinal arcuate component 182b defining an edge or border of the second interior dimple 180b.

In certain embodiments, the thickness of the portion of the distance of the elongated cylindrical wall 131 may be thinnest at the lateral center for each of the corresponding interior dimples 180a, 180b. For example, the thickness of the lateral center for each of the corresponding interior dimples 180a, 180b may be dimensioned to have length (D4-12) of approximately 0.013 inches. In other embodiments, each of the interior dimples 180a, 180b may be arranged to have different thicknesses at its corresponding lateral center. For example, the lateral center of the first interior dimple 180a may be formed such that it extends into the elongated cylindrical wall 131 a distance (D4-13) of approximately 0.110 inches from the axial center or central longitudinal axis 501.

Moreover, in some implementations, lateral radial components for which the interior dimples 180a, 180b are formed may be based from offset axes parallel to the central longitudinal axis 501. For example, the first interior dimple 180a may be formed based on an offset axis that is a length (D4-9) of approximately 0.010 inches toward the first interior dimple 180a, and the second interior dimple 180b may be formed based on an offset axis that is a length (D4-11) of approximately 0.015 inches toward the second interior dimple 180b.

FIG. 4B is a lateral cross-sectional view of the compressible valve 100 along section line C-C of FIG. 3C at which the first internal dimple 180a is disposed. As discussed above, the first internal dimple 180a may be formed based on an offset axis that is a length (D4-9) of approximately 0.010 inches from the central longitudinal axis 501 the toward a central region of the first interior dimple 180a (e.g., corresponding to a thinnest portion of the interior wall 132). A varying lateral thickness of the portion of the interior wall 132 having the first internal dimple 180a disposed thereon is illustrated in FIG. 4B. An exemplary concave shape of the first internal dimple 180a can be understood with reference to the varying longitudinal thickness of the portion of the interior wall 132 having the first internal dimple 180a disposed thereon, as illustrated in FIG. 4A.

Configuring elliptically and concave shaped interior dimples 180a, 180b on the interior wall 132 as provided herein can aid in proper compressing (e.g., an initial bowing out of the interior dimple proximal to its lateral center) and subsequent collapsing, canting, and/or folding of the lower portion 130 of the compressible valve 100 during operation of an assembled needleless connector.

FIG. 5A is an enlarged longitudinal cross-sectional view of the flange portion 135 at detail region D of FIG. 4A. The flange portion may include an inwardly facing lip 137 for interfacing with a valve mount of a needleless connector housing, for example. The inwardly facing lip 137 may extend along the entirety of the circumferential edge of the flange portion 135. In certain embodiments, the inwardly facing lip 137 may be dimensioned to have an angle (D5-1) of approximately 9° with respect to a lateral or transverse plane of the flange portion 135 (i.e., with respect to a plane perpendicular to central longitudinal axis 501).

FIG. 5B is an enlarged longitudinal cross-sectional view of the lower portion 130 of the compressible valve 100 at detail region E of FIG. 4A. The elongated cylindrical wall 131 may have an exterior diameter (D5-2) of approximately 0.245 inches and an interior diameter (D5-3) of approximately 0.185 inches. Moreover, the flange portion 135 may have a length (D5-4) of approximately 0.110 inches.

Embodiments of the compressible valve 100 may comprise any of the various materials used for producing mechanical valves for needleless connectors and other medical implements. In some implementations, the head 110 may be comprised of an elastomeric material, such as but not limited to, a silicone compound. Moreover, the primary seal portion 120 and lower portion 130 may comprise an elastomeric material. For example, in some implementations, the head 110 and primary seal portion 120 may have a durometer value of approximately 70+/−5 on a Shore A hardness scale. In certain implementations, all or some of the compressible valve 100 may be comprised of liquid silicone rubber of the Wacker ELASTOSIL® LR 3003 Series having a Shore A hardness durometer value of 70+/−5.

Additionally, in some embodiments, the elastomeric material of the head 110 and/or primary seal portion 120 may have a higher durometer value than the elastomeric material of the lower portion 130. For example, the collapsing functionality of the lower portion associated with facilitating a fluid flow path in the needleless connector may benefit from a more pliable material for operation, whereas the head and primary seal portion may require a more rigid construction for disengaging the primary seal.

Figure 6A:
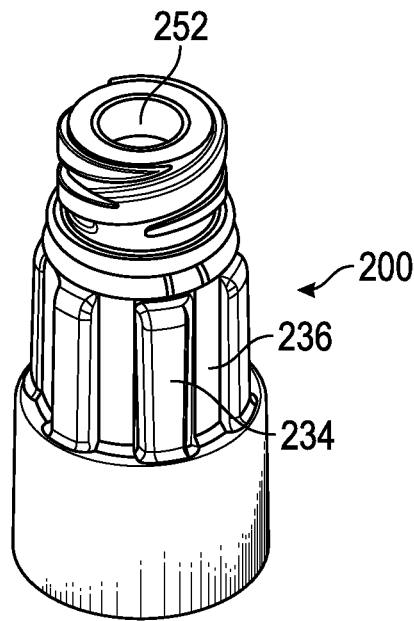
FIGS. 6A and 6B are perspective views illustrating an example of a body portion of a housing, in accordance with aspects of the present disclosure.
Figure 6C:
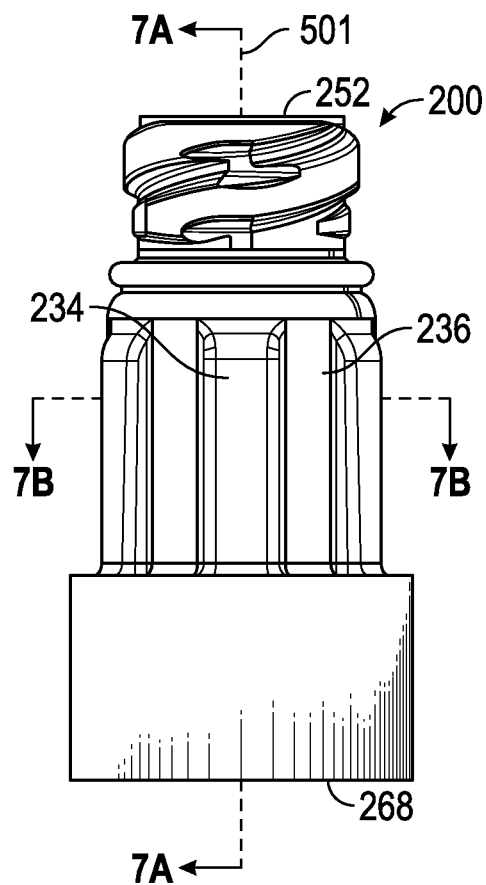
FIG. 6C is a front plan view illustrating an example of a body portion of a housing, in accordance with aspects of the present disclosure.
Figure 6B:
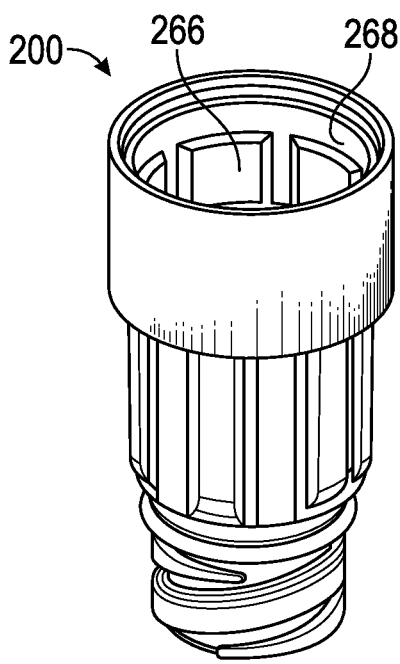

FIGS. 6A to 6C illustrate an example body portion 200 of a housing. Body portion 200 may comprise a first port 252 for interfacing with a medical implement and an opening 268 for connecting with a base portion of the housing. Body portion 200 may comprise one or more fluid flow channels 234 and one or more interior support columns 236. The lower section of the body portion 200 (e.g., a section proximal to the opening 268) may have an increased diameter and include one or more internal contact tabs 266. When assembled in a needleless connector, the one or more internal contact tabs 266 provide a radial force substantially orthogonal to the central longitudinal axis 501 onto a flange portion of a compressible valve that is arranged on a valve mount of the base portion.

Figure 7A:
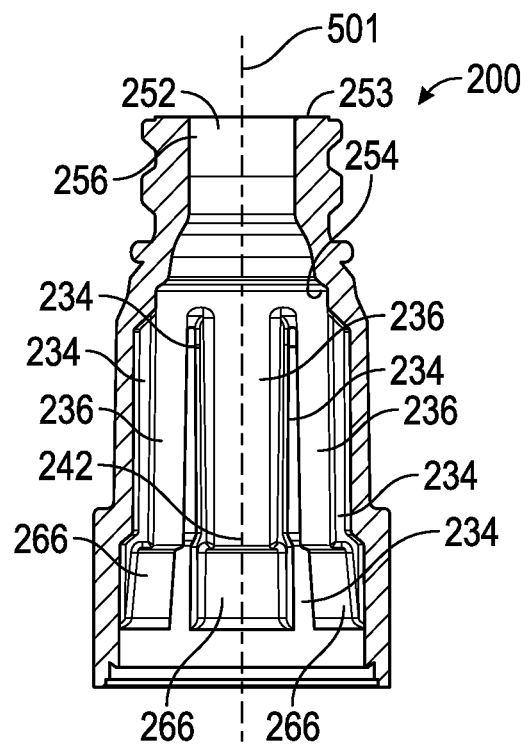
FIGS. 7A and 7B are cross-sectional views illustrating an example of a body portion of a housing, in accordance with aspects of the present disclosure.
Figure 7B:
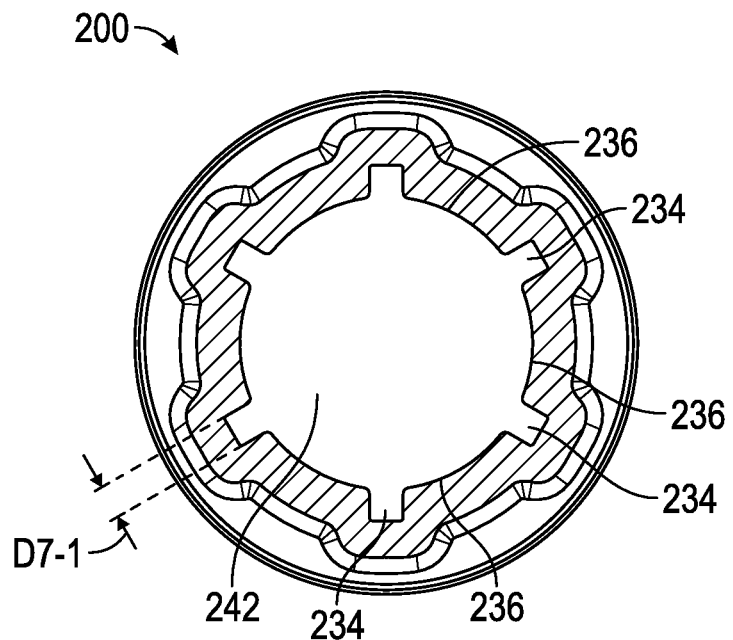

FIG. 7A is a longitudinal cross-sectional view of the body portion 200 along section line F-F of FIG. 6C. The first port 252 may include a top port surface 253 and a port channel 256. The first port 252 may include engagement features for coupling to another device (e.g., fluid transfer assembly). For example, engagement features may include cooperating mechanical elements, such as internal or external surface threads, detents, bayonet-type locking elements, etc., as well as other surface configurations, such as a tapered Luer surface for frictional engagement. In certain embodiments, the first port 252 can include a female luer fitting with luer lock threading.

The body portion may include an internal cavity 242 and an internal sealing edge 254. The internal sealing edge 254 may be a circumferential edge and configured for retaining a compressible valve within the internal cavity 242 of an assembled needleless connector. In operation, the internal sealing edge 254 may be arranged to provide blocking of fluid flow in conjunction with a primary seal portion of the compressible valve.

In certain embodiments, fluid flow channels 234 may alternate with interior support columns 236. This configuration is further illustration in FIG. 7B, which provides a lateral cross-sectional view of the body portion 200 along section line G-G of FIG. 6C. In certain embodiments, fluid flow channels 234 may be smaller than the interior support columns 236. For example, a fluid flow channel may be dimensioned to have a cross-sectional length (D7-1) of approximately 0.031 inches. In an assembled needleless connector, a top edge portion of a head of a compressible valve that is disposed above a notch in the head may be arranged such that each top edge portion 414a, 414b is aligned with an interior support column 236 (e.g., where the top edge portion 414a effectively straddles two radially consecutive fluid flow channels 234 and the top edge portion 414b effectively straddles two radially consecutive fluid flow channels 234 on opposite sides of the body portion). Thus, in smaller dimensioned needleless connectors, blockage of a fluid flow path and/or damage to the top edge and notch of the head and/or a portion of the frustoconical surface/primary seal disposed proximal to the notch from continued contact with a longitudinally transition edge formed between an adjacent flow channel 234 and interior support column 236 can be avoided by such an arrangement.

Additionally, fluid flow channels 234 may further extend into the lower portion of the body portion 200 between adjacent internal contact tabs 266 (FIG. 7A). In this regard, a fluid path may be extended to a base portion of the housing coupled to the body portion 200 and further to a second port.

FIGS. 8A to 8D illustrate in isolation an example base portion 300 of a housing. The base portion 300 may comprise a second port 382 for interfacing with a medical implement and a valve mount 355. The valve mount 355 may comprise a rim 350 that defines a recess 340 with one or more air passages 372. The base portion 300 may comprise one or more fluid passages 374 for completing a fluid flow path from the internal cavity and fluid flow channels of the body portion to the second port 382 of the base portion 300. The rim 350 of the valve mount 355 may include an upper partial transverse wall 353 (e.g., partially extending in a plane transverse to the central longitudinal axis 501) and a lower partial transverse wall 357.

The base portion 300 is dimensioned to be coupled to and fused with the body portion 200 to create a housing of a needleless connector. For example, the base portion 300 at its thickest section may be dimensioned to have a diameter (D8-1) of approximately 0.455 inches. Additionally, the base portion 300 may be dimensioned to have a length (D8-2) of approximately 0.505 inches.

Figure 8C:
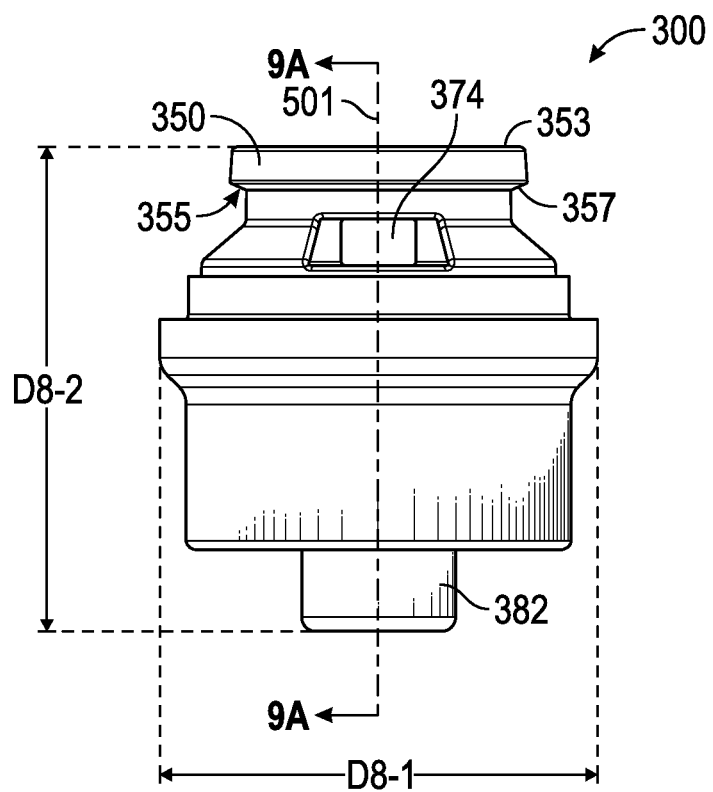
FIGS. 8C and 8D are front plan views illustrating an example of a base portion of a housing, in accordance with aspects of the present disclosure.

FIG. 9A is a longitudinal cross-sectional view of the base portion 300 along section line H-H of FIG. 8C. The second port 382 may include engagement features for coupling to another device or to interconnect tubing. For example, the second port 382 may comprise a male luer-taper fitting and luer lock threading 384 for medical device implement interconnection. However, engagement features of the second port 382 may include other cooperating mechanical elements. The one or more fluid passages 374 are configured to be fluidly coupled to the internal cavity 242 via the one or more fluid flow channels 234 (e.g., when the housing is assembled) and to complete a fluid flow path to the second port 382.

Figure 8D:
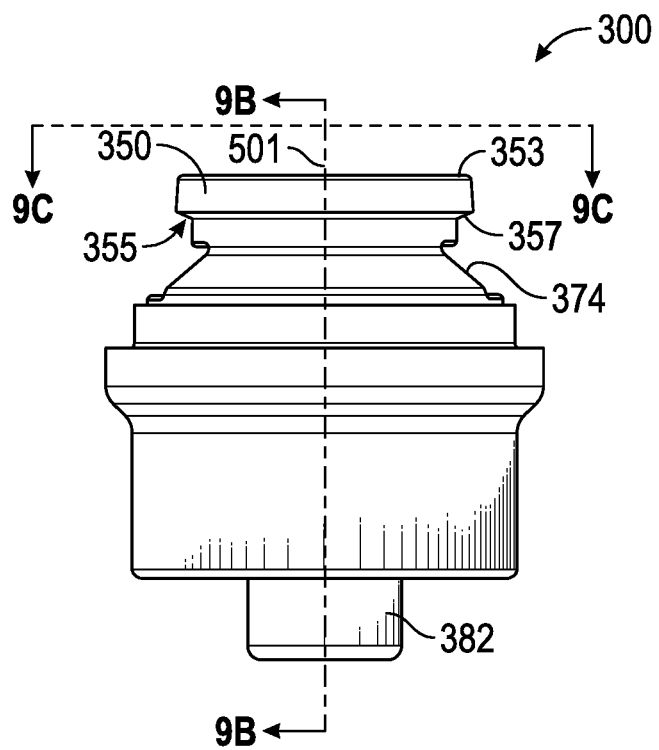

FIG. 9B is a longitudinal cross-sectional view of the base portion 300 along section line J-J of FIG. 8D. Air passage channels 372 may facilitate an air flow path from an internal air space of the compressible valve 100 (e.g., when the compressible valve 100 is coupled to the valve mount 355 and secured within the housing) to a connected device (e.g., via luer lock threading 384) or to ambient environment. FIG. 9C is a lateral overhead view of the base portion 300 along section line K-K of FIG. 8D. The base portion 300 may include one or more support members 380 that extend from the rim 350 laterally into the recess 340. When assembled, a top surface of the rim 350 (e.g., the upper partial transverse wall 353 and the one or more support members 380) may contact with the flange portion 135. The recess 340 includes a bottom surface 360 that is distally separated from the top surface of the rim 250. The bottom surface in cooperation with other aspects of the base portion 340 can also provide a barrier between the fluid pathways (e.g., one or more fluid passages 374) and the air flow paths (e.g., air passage channels 372).

FIG. 10 provides a longitudinal cross-sectional view of needleless connector 10 showing the compressible valve 100 in the housing formed by the body portion 200 and the base portion 300. The cross-sectional view of FIG. 10 is of the needleless connector 10 along section line A-A of FIG. 1C. The assembled needleless connection 10 as illustrated in FIG. 10 is in a sealed configuration such that any fluid from an interconnected fluid path coupled to the second port 382 is sealed from the first port 252.

Needleless connector 10 may be assembled such that the flange portion 135 of the compressible valve 100 (FIGS. 3A to 5B) is coupled or snapped onto the valve mount 355 of the base portion 300. For example, the flange portion 135 may include an inwardly facing lip 137 and partial transverse upper wall abutting the elongated cylindrical wall 131 such that the flange portion 135 can securely engage with the valve mount 355. The rim 350 of the valve mount 355 may include an upper partial transverse wall 353 and a lower partial transverse wall 357 to facilitate such a secure engagement with the flange portion 135 and compressible valve 100.

The opening 268 of the body portion 200 (FIGS. 6A to 7B) may be arranged on top of the compressible valve 100 coupled to the base portion 300 such that the head 110 of the compressible valve 100 is aligned and disposed within the port channel 256 of the first port 252. Upon assembly, the top surface 116' of the head 110 of the compressible valve 100 has a resulting plane that is substantially perpendicular to the central longitudinal axis 501 or axial center of the column section 118 of the head 110 when the head 110 is engaged within the port channel 256 of the housing. Additionally, the one or more internal contact tabs 266 disposed on the lower section of the body portion 200 surround and apply pressure to a sidewall of the flange portion 135 to secure or anchor the compressible valve 100 in the housing. In operation, the compressible valve 100 of the needleless connector can compress and collapse when an axial force is applied to the top surface 116' of the compressible valve 100 and expand and realign when the axial force is removed.

Accordingly, the one or more internal contact tabs 266 provide a radial force 525 substantially orthogonal to the central longitudinal axis 501 onto the sidewall of the flange portion 135 and the rim 350 of the base portion 300. In this regard, when an axial force is applied to the top surface 116' of the head 110 of the compressible valve 100, the effect of any resulting axial force through the compressible valve 100 onto the base portion 300 is reduced if not eliminated. Such a resulting axial force applied onto the base portion 300 can work against or in derogation to the fused connection 550 of the base portion 300 and the body portion 200, and over time may cause the fused connection 550 to become breached and/or separated.

Figure 11A:
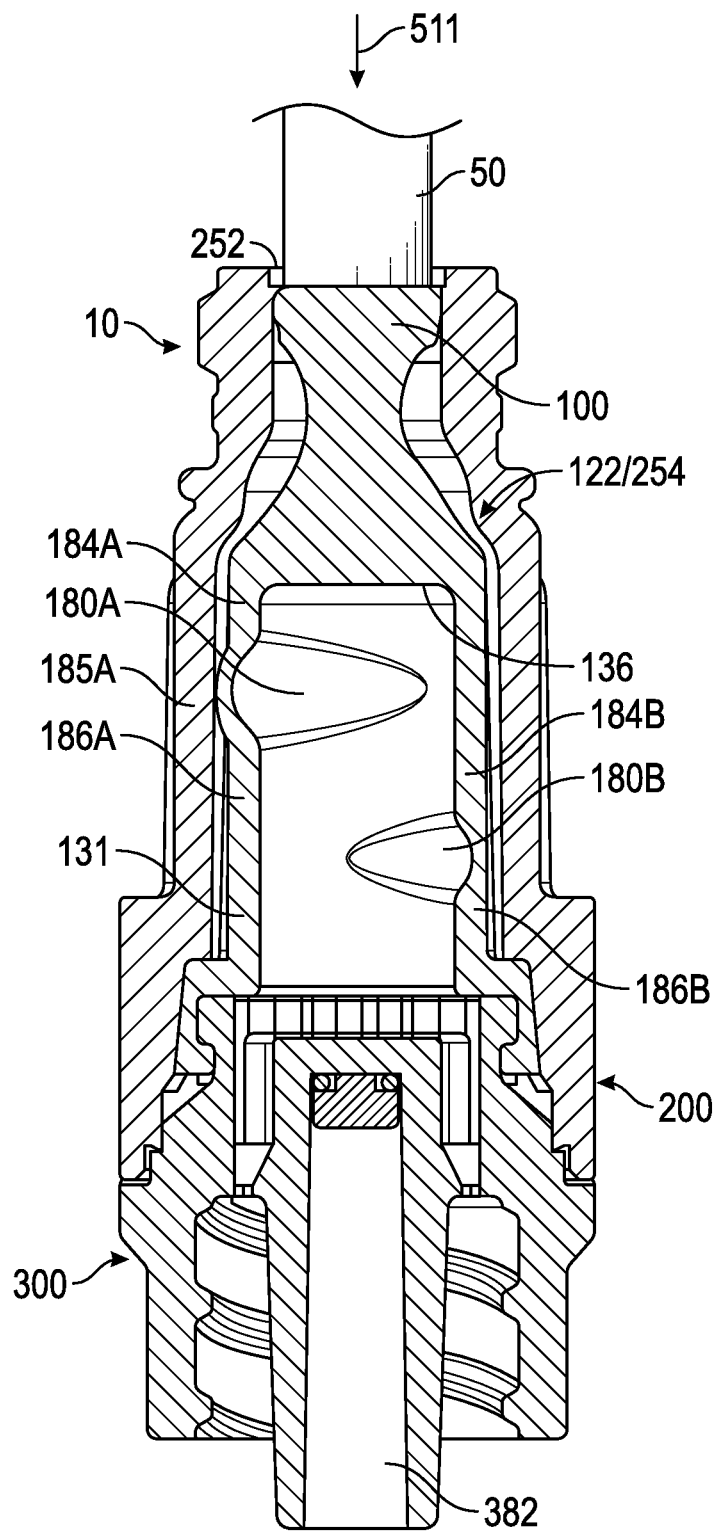
FIGS. 11A and 11B are a cross-sectional views illustrating an example of a needleless connector in use, in accordance with aspects of the present disclosure.

FIG. 11A provides a longitudinal cross-sectional view of needleless connector 10 showing the compressible valve 100 upon initial entry of a medical implement 50 into the first port 252. The cross-sectional view of FIG. 11A is of the needleless connector 10 along section line A-A of FIG. 1C as would be modified by the described valve operation.

As medical implement 50 (e.g., an syringe) is initially inserted into the first port 252 of the needleless connector 10, an initial axial force 511 is exerted onto the compressible valve 100 such that a central portion 185a of the elongated cylindrical wall 131 proximal to the first interior dimple 180a may slightly bow out toward the inner wall of the body portion 200 (e.g., the fluid flow channels 234 and interior support columns 236). Additionally, the frustoconical surface 122 of the primary seal portion 120 may separate from the internal sealing edge 254.

Figure 11B:
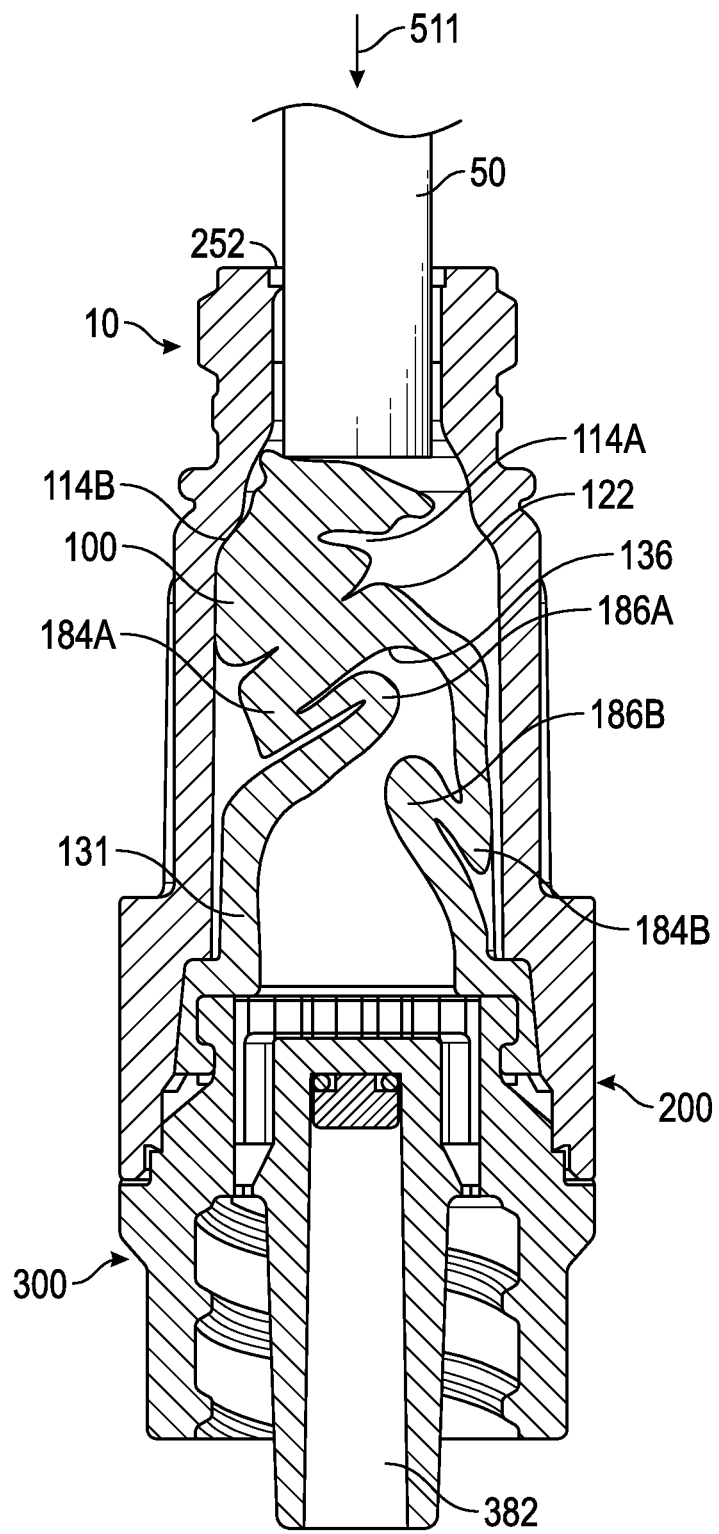

FIG. 11B provides a longitudinal cross-sectional view of needleless connector 10 showing the compressible valve 100 after further entry of the medical implement 50 into the first port 252. The cross-sectional view of FIG. 11A is of the needleless connector 10 along section line A-A of FIG. 1C as would be modified by the described valve operation.

Upon additional axial force 511, the medical implement 50 descends further into the first port 252, further compressing, collapsing, canting, and/or folding may occur with respect to certain sections of the compressible valve 100. For example, as illustrated in FIG. 11B, a bottom portion 186a of the elongated cylindrical wall 131 proximal to the first interior dimple 180a may fold inwardly and underneath a top portion 184a. Similarly, a bottom portion 186b of the elongated cylindrical wall 131 proximal to the second interior dimple 180b may fold inwardly and underneath a top portion 184b.

Additionally, the first notch 114a may fold or collapse and the second notch 114b may open or expand such that the first top edge portion 414a may tilt downwardly. In this regard, a fluid path from the medical implement 50 in the first port 252 may be established through the interior of the needleless connector 10 to the second port 382. For example, a fluid path may be established between the first port 252 and the second port 382 via the internal cavity 242 and the fluid flow channels 234 (FIGS. 6B, 7A, and 7B), to the base portion 300 and through fluid passages 374, and into the second port 382 (FIGS. 8A, 8C, and 9A).

Moreover, as discussed above, the second top edge portion 414b, the second notch 114b, and/or a portion of the frustoconical surface 122 disposed proximal to the second notch 114b may be positioned such that they predominantly contact an interior support column 236 of the body portion 200 (FIGS. 7A and 7B) while in the compressed configuration.

When the medical implement 50 is removed from the first port 252, the compressible valve 100 may return to its position within the housing in the sealed configuration as illustrated in FIG. 10.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector comprising:
   a housing defining an internal cavity and a central longitudinal axis, the housing comprising:
      a body section comprising a first port and an inner surface having support columns and contact tabs, wherein the support columns are longitudinally aligned with the contact tabs, and the support columns and the contact tabs are spaced apart from adjacent support columns and contact tabs to define a fluid flow channel therebetween, and
      a base section comprising a valve mount at a top of the base section and a second port at a bottom of the base section, the valve mount comprising a valve mount rim extending away from the central longitudinal axis; and
      a compressible valve comprising a valve wall and a flange protruding radially outward from an outer surface of the valve wall, the flange comprising an outer surface and an inner surface, wherein, when the compressible valve is coupled with the base section, the valve mount rim engages against the inner surface of the flange, and the contact tabs engage against the outer surface of the flange.

2. The needleless connector of claim 1, wherein the flange comprises a channel that extends into the inner surface of the flange, toward the outer surface of the flange.

3. The needleless connector of claim 1, wherein the valve wall comprises a first dimple and a second dimple formed in an internal surface.

4. The needleless connector of claim 1, wherein base section comprises a recess between the valve mount and the second port.

5. The needleless connector of claim 4, wherein support members extend laterally inward from the valve mount into the recess.

6. The needleless connector of claim 4, wherein the valve mount rim extends from an upper wall of the valve mount toward the bottom of the base section.

7. The needleless connector of claim 1, wherein a cross-sectional width of the internal cavity along the contact tabs is greater than a cross-sectional width of the internal cavity along the support columns.

8. The needleless connector of claim 1, wherein the base section comprises a fluid passage extending through an outer surface of the base section, between the valve mount and the bottom of the base section, and wherein the fluid passage extends through the second port.

9. A needleless connector comprising:
a housing defining an internal cavity and a central longitudinal axis, the housing comprising:
a body section comprising a first port and an inner surface having support columns and contact tabs, wherein the support columns are longitudinally aligned with the contact tabs, and the support columns and the contact tabs are spaced apart from adjacent support columns and contact tabs to define a fluid flow channel therebetween, and
a base section comprising a valve mount at a top of the base section and a second port at a bottom of the base section, the valve mount comprising a valve mount rim; and
a compressible valve comprising a valve wall and a flange protruding radially outward from an outer surface of the valve wall, the flange comprising an upper lip, a lower lip, and a flange rim, wherein, when the compressible valve is coupled with the base section, the fluid flow channel extends between an outer surface of the flange rim and the contact tabs.

10. The needleless connector of claim 9, wherein the lower lip is spaced apart from the upper lip.

11. The needleless connector of claim 9, wherein a channel is formed between an inner surface of the upper lip and an inner surface of the lower lip.

12. The needleless connector of claim 9, wherein a cross-sectional width of the outer surface of the flange rim tapers from the lower lip toward the upper lip.

13. The needleless connector of claim 9, wherein a height of the lower lip decreases from the flange rim toward the central longitudinal axis.

14. The needleless connector of claim 9, wherein when the compressible valve is coupled with the base section, the flange rim is compressed between the valve mount and the contact tabs.

15. The needleless connector of claim 9, wherein the valve wall comprises a first dimple and a second dimple formed in an internal surface.

16. The needleless connector of claim 9, wherein base section comprises a recess between the valve mount and the second port.

17. The needleless connector of claim 16, wherein support members extend laterally inward from the valve mount into the recess.

18. The needleless connector of claim 17, wherein the support members extend between an upper wall of the valve mount and a bottom surface of the recess.

19. The needleless connector of claim 9, wherein the valve mount rim extends from an upper wall of the valve mount toward the bottom of the base section.

20. The needleless connector of claim 9, wherein a cross-sectional width of the internal cavity along the contact tabs is greater than a cross-sectional width of the internal cavity along the support columns.

* * * * *